United States Patent [19]

Winstead-Hall

[11] 4,356,822

[45] Nov. 2, 1982

[54] SYRINGE ASSEMBLY

[76] Inventor: Deborah Winstead-Hall, 6747 Townbrook Dr., Apt. D, Baltimore, Md. 21207

[21] Appl. No.: 198,056

[22] Filed: Oct. 17, 1980

[51] Int. Cl.³ ............................................. A61M 5/00
[52] U.S. Cl. .................................. 128/215; 128/218 R
[58] Field of Search .......... 128/218 R, 218 N, 218 F, 128/215, 220, 221

[56] References Cited

U.S. PATENT DOCUMENTS

| | | | |
|---|---|---|---|
| 1,436,707 | 11/1922 | Gaschke. | |
| 2,091,438 | 8/1937 | Epstein | 128/221 |
| 2,554,451 | 5/1951 | Barry | 128/220 |
| 2,556,331 | 6/1951 | Lockhart | 128/220 |
| 2,568,346 | 9/1951 | Lockhart | 128/220 |
| 2,578,812 | 12/1951 | Kollsman | 128/220 |
| 2,845,065 | 7/1958 | Gabriel | 128/215 |
| 3,073,306 | 1/1963 | Linder | 128/215 |
| 3,399,675 | 9/1968 | Hill | 128/215 |
| 3,434,473 | 3/1969 | Smith | 128/221 |
| 3,527,216 | 9/1970 | Snyder | 128/218 |
| 3,605,743 | 9/1971 | Arce | 128/218 F |
| 3,702,609 | 11/1972 | Steiner | 128/218 F |
| 3,739,780 | 6/1973 | Ogle | 128/220 |

FOREIGN PATENT DOCUMENTS

| | | | |
|---|---|---|---|
| 1500058 | 11/1967 | France | 128/218 F |
| 543518 | 3/1956 | Italy | 128/218 F |

*Primary Examiner*—John D. Yasko
*Attorney, Agent, or Firm*—Buell, Blenko, Ziesenheim & Beck

[57] ABSTRACT

A syringe assembly having a hollow barrel and a needle in communication with the barrel for receipt or discharge of material therethrough. A plunger is received within the hollow barrel. A cap member receives at least a portion of the barrel and locking members are provided for securing the barrel and cap in a number of relative axial positions. A frangible end closure may be provided on the end of the cap closest to the needle. The locking members permit different locked positions for exposing different amounts of the needle. The locking members may be formed on the barrel and cap and may consist of a series of formations on the barrel adapted to engage a series of formations on the cap. Ready locking and unlocking is permitted.

12 Claims, 6 Drawing Figures

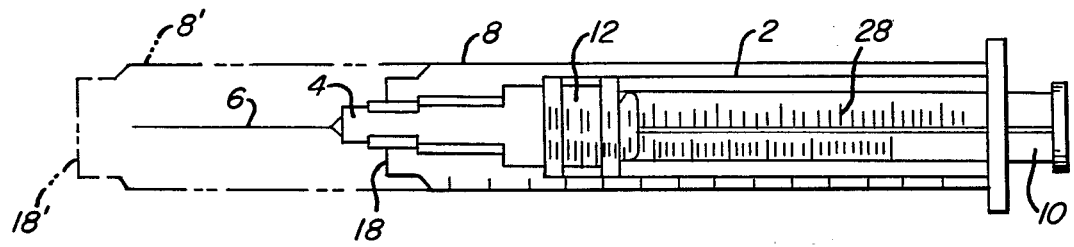
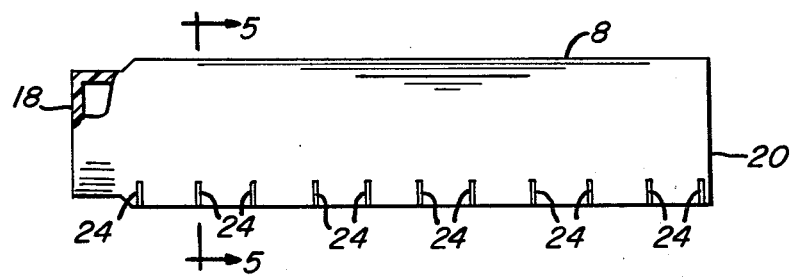
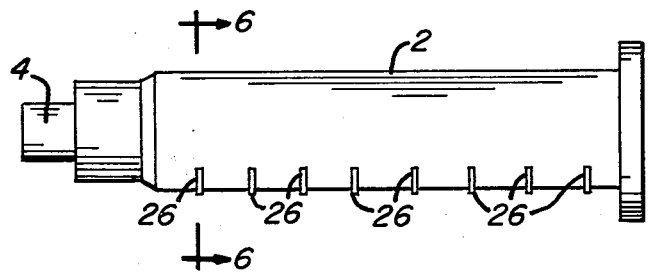
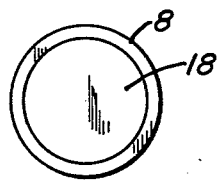 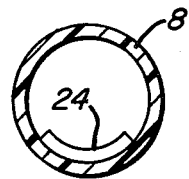 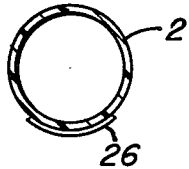

SYRINGE ASSEMBLY

BACKGROUND OF THE INVENTION

1. Field of the Invention

This invention relates to a syringe assembly, and, more specifically, relates to such an assembly which is adapted to have improved safety and efficiency features when used in a medical environment, as well as other environments.

2. Description of the Prior Art

Various types of syringe assemblies for receiving and dispensing medication as well as other materials have been known. In general, the medication or other material is introduced into the hollow barrel portion either by receiving the same through the needle which communicates with the barrel interior, or by means of a frangible container, such as an ampule, which is placed within the hollow barrel. Applying pressure to the plunger causes the medication or other material to be expressed through the hollow needle.

It has been known to provide means for controlling the dosage of medicinal compositions dispensed by a hypodermic syringe through the use of adjustable means. See U.S. Pat. Nos. 2,554,451 and 2,578,812.

Various means have been suggested for controlling the depth of needle penetration into a patient. U.S. Pat. No. 3,434,473 discloses multiple closures, with the removal of each resulting in an additional amount of the needle being exposed. U.S. Pat. Nos. 1,436,707 and 2,091,438 disclose the use of mechanical stop members secured directly to the needle.

A number of disclosures provide means for detecting seepage of blood through the needle bore. See U.S. Pat. Nos. 2,556,331, 2,568,346 and 3,739,780.

U.S. Pat. No. 3,527,216 discloses a multi-compartment mixing chamber wherein the needle is said to serve as a means for fracturing seals to initially mix components which are sealed separately and ultimately to administer the mixture.

There remains a very substantial need for a syringe assembly which will easily and effectively permit adjustment of depth of needle penetration while resisting undesired accidental puncture wounds during syringe handling, use and disposal.

SUMMARY OF THE INVENTION

The present invention has met the above-described need by providing a syringe assembly which has a hollow barrel, needle means in communication with the barrel, plunger means received within the hollow barrel and cap means for receiving at least a portion of the barrel. Locking means are provided for securing the barrel and cap means in a number of relative axial positions which correspond with various depths of needle penetration. The locking means advantageously may be integrally formed on the barrel and cap means and permit ready locking and unlocking for initial needle exposure, receipt of medication, administering of medication and safe disposal of the syringe.

It is an object of this invention to provide a syringe assembly which is adapted to permit ready locking of a cap means and a barrel in a number of different axial positions.

It is a further object of the present invention to so establish the locking relative barrel-cap means positions as to permit variations in the extent of needle exposure.

It is a further object of the present invention to permit locking of the barrel and cap means in such position as to avoid needle exposure prior to use of the syringe and after such use has been completed.

It is a further object of the present invention to provide such an assembly which is adapted to provide improved sterility by avoiding superfluous needle exposure to both the patient and others handling the syringe.

It is a further object of the present invention to provide such a syringe assembly which is adapted for use in accordance with standard accepted procedures.

These and other objects of the invention will be more fully understood from the following description of the invention on reference to the illustrations appended hereto.

BRIEF DESCRIPTION OF THE DRAWINGS

FIG. 1 is a partially schematic illustration of one form of syringe assembly of the present invention.

FIG. 2 is the partially broken away front elevational view of one form of cap means of the present invention.

FIG. 3 is a front elevational view of a form of barrel means of the present invention.

FIG. 4 is a left-side elevational view of the cap means shown in FIG. 2.

FIG. 5 is a cross-sectional illustration of the cap means of FIG. 2 taken through 5—5.

FIG. 6 is a cross-sectional illustration of the syringe barrel of FIG. 3 taken through 6—6.

DESCRIPTION OF THE PREFERRED EMBODIMENTS

While for convenience of reference and simplicity of disclosure herein, specific reference will be made to syringe assemblies which are used on humans and animals, primarily for dispensing medicinal preparations, it will be appreciated that other uses including, but not limited to, industrial and residential uses may advantageously be made of the present invention.

Referring now in greater detail to FIG. 1, there is shown a general arrangement of a form of syringe assembly of the present invention. A hollow barrel 2, which in the form shown is substantially cylindrical, terminates in a needle support 4 which secures tubular needle 6 thereto. The hollow needle 6 is in communication with the hollow interior of barrel 2. A cap member 8, which will be described in greater detail below is, in the form shown, substantially cylindrical and has a diameter larger than the external diameter of the barrel. The barrel 2 is at least partially received within the cap 8. A plunger 10 having a piston 12 is received within the barrel and manually employed to discharge material through needle 6 and, may also be employed to introduce material into the barrel through needle 6.

The present invention contemplates providing locking means for securing the barrel 2 and cap member 8 in a plurality of relative axial positions.

In a preferred embodiment of the invention, the cap means 8 has a first end which is provided with end wall 18 and a second end 20 which is open. The end wall 18 is frangible so as to be pierced by the needle 6. End wall 18 may be integrally formed or, alternatively, may be secured as a separate member. It is contemplated that during storage of the syringe assembly, prior to use, undesired contamination of the needle 6 will be resisted by locking the cap means 8 in the position shown in the dotted form as cap means 8′ in FIG. 1. In this position, the free end of needle 6 is preferably spaced from end wall 18'.

In the embodiment illustrated in FIGS. 2 and 5, the cap means 8 has a plurality of generally circumferentially oriented radially inwardly projected ribs 24 which are preferably spaced equidistant from the next adjacent rib or ribs. In a preferred embodiment of the invention, the spacing between a pair of adjacent ribs 24, measured axially of the cap means 8, will be about $\frac{1}{8}$ to $\frac{3}{8}$ inch. It is also noted that the rib 24 extends circumferentially less than 180° and preferably less than 90° about the circumference.

Finally, it is preferred that the ribs 24 be substantially aligned with each other in order to facilitate locking and unlocking between the cap means 8 and the barrel 2. In the form shown, eleven ribs 24 have been provided. Ribs 24 are preferably substantially of the same circumferential length.

Referring now in greater detail to FIGS. 3 and 6, it is noted that, in the form shown, the barrel member 2 has a plurality of radially outwardly projecting generally circumferentially oriented ribs 26. These ribs 26 extend circumferentially less than about 180° about the circumference of the barrel 2 and preferably less than about 90° about the circumference. In the form shown, eleven ribs 26 have been illustrated. These ribs 26 are preferably spaced substantially uniformly with respect to each other with the spacing between a pair of adjacent ribs 26 preferably being about $\frac{1}{8}$ to $\frac{3}{8}$ inch and preferably being the same as the spacing between adjacent ribs 24. Ribs 26 are preferably substantially of the same circumferential length and are generally aligned with each other so as to facilitate relative locking and unlocking of the assembly.

With respect to the relative heights of ribs 24 and 26, there is no critical dimension, however, the combined heights must be such as to produce sufficient mechanical interference contact as to resist relative axial movement of the barrel 2 with respect to the cap means 8 when ribs 24 are aligned with ribs 26.

It will be appreciated, that while a preferred, specific form of locking means has been illustrated, other forms of locking means will be apparent to those skilled in the art. It will be appreciated that a specific preferred embodiment of the invention involving a barrel with outwardly projecting circumferential ribs and a cap with inwardly projecting circumferential ribs has been shown and described, other locking means will be apparent to those skilled in the art. For example, the locking means may all be outwardly projecting on both the barrel and cap with one being made of resilient material. Also, the locking means need not take the form of circumferential ribs. Means which serve to provide for relative locking between the barrel 2 and cap means 8 in a plurality of different relative axial positions so as to resist relative axial movement may be employed. For example, a series of ribs on one of the two members 2, 8 may be adapted to fit into grooves on the other member. Also, the circumferential extent of the ribs or grooves may be different on one member than on the other. Further, obstruction means which are adapted to be engaged and disengaged may be oriented in directions other than circumferentially or the individual developments may be symmetrical and lack specific orientation. Further, while in the form shown, it is preferred that the ribs 24, 26 be integrally molded and preferably of solid cross section and that the cap means and barrel means be substantially rigid, it will be appreciated that the use of resilient materials may also be permitted. For example, continuous annular ribs on one member may be engaged with continuous or discontinuous members on the other with locking and unlocking be effected by applying meaningful force in a relative axial direction so that a resilient member may expand to overcome the locking resistance to relative axial movement and resume its reduced radial dimension to effect locking at another position.

In operation of the preferred embodiment illustrated, one would start with the cap in the position shown at 8' in FIG. 1. By moving the ribs 24, 26 to relative nonaligned, noninterfering relationship by relative axial rotation, the cap 8' may be moved into relative closing relationship with the barrel member 2 thereby permitting the needle 6 to puncture end wall 18'. When the desired relative axial position between the cap means 8 and the barrel means 2 has been attained, relative rotation is effected in order to align ribs 24 with ribs 26 thereby locking the cap 8 in the desired position with respect to barrel 2. While a certain degree of "play" is permitted to the extent of the spacing between ribs 24 and ribs 26, it will be appreciated that movement will be resisted upon contact between ribs 24 and 26. If desired, for a specific use, the spacing between adjacent ribs 24, 26 on one or both members 2, 8 may be reduced so as to minimize or generally eliminate "play". Assuming that this first positioning provides a first extent of needle projection desired for filling the syringe, the needle 6 may be introduced into a container which houses the medicinal or other materials sought to be introduced to the syringe and the plunger moved outwardly so as to permit filling of the hollow barrel with the desired volume. If at this point it is desired to assume a different depth of needle exposure for introduction of the medicinal material into a patient, relative rotation between the barrel 2 and the cap means 8 is effected to unlock the two components, relative axial movement is established therebetween and rotation to effect locking then takes place. The medicine may then be administered in safe fashion.

Alternatively, if it is desired to insert an ampule into the hollow barrel interior, the plunger 10 and associated piston 12 may be removed from the barrel to permit introduction of the ampule which will be crushed upon applying pressure to the plunger 10. Prior to crushing the ampule, the extent of desired needle exposure may be established.

After use, in order to avoid the hazard of inadvertent puncture wounds on the syringe user or those handling disposal of trash, the cap means 8 may be unlocked and subjected to relative separating axial movement from the barrel 2 so as to assume a position similar to position 8' in FIG. 1 thereby shielding the point of needle 6.

While the barrel 2 and cap means 8 of the present invention may be made of any suitable material, among the specifically preferred material are glass and plastic.

As is shown in FIG. 1, graduation marks 28 may advantageously be applied to the barrel, as by hot etching the barrel exterior or other means. Hot etching of graduations reduces likelihood that the relative twisting action will rub off the graduations.

It will be appreciated that the present invention offers effective and precise control of depth of needle penetration thereby minimizing the risk of undesired hitting of a nerve or bone during injection of a medicinal substance into a patient. The plurality of locked positions permits ready adaptation to body size of the patient, as well as injection site.

It will further be appreciated that sterility is further enhanced by eliminating the need to expose the entire needle during drawing up of medication from another container.

The person drawing the medication is unable to contact other portions of the needle, but rather would hold the cap means 8 instead. As a result of minimizing undesired puncture wounds by the user as well as those subsequently handling the syringe assembly, not only is an undesired health hazard and lost time from employment minimized, but also the expense of treating such wounds and providing substitute employees is eliminated. There are further advantages in the nature of psychological advantages. The user feels more confident that the hazards of undesired puncture will be avoided and the person receiving the injection needn't see any more exposed needle than is essential for the particular purpose.

The invention further eliminates the need to change needles after drawing medication due to possible difference in exposed needle length needed on drawing medication from needed length at the injection site.

Whereas particular embodiments of the invention have been described, for purposes of illustration it will be evident to those skilled in the art that numerous variations of the details may be made without departing from the invention as defined in the appended claims.

I claim:

1. A syringe assembly comprising
   a hollow barrel,
   needle means fixedly secured to and in communication with said barrel and having a free end of discharge of material therefrom,
   plunger means received within said hollow barrel,
   said plunger means being movable manually to discharge material from said needle means,
   cap means for receiving at least a portion of said barrel,
   locking means for securing said barrel and said cap means in one of a number of relative axial positions, while permitting relative movement of said plunger means with respect to said barrel and said cap means,
   said locking means permitting a locked position of said cap means and said barrel means in a plurality of positions permitting needle shielding by said cap means and different needle exposure beyond said cap means first end, whereby depth of needle penetration may be controlled,
   said locking means includes cooperating means formed on said barrel and on said cap means, and
   said needle means free end having a predetermined position with respect to said cap means for each said locked relative axial position of said barrel and said cap means, whereby said free end may be shielded by said cap means or project a predetermined distance therebeyond depending upon said locked relative axial positions of said cap means and said barrel and independent of the relative position of said plunger means.

2. The syringe assembly of claim 1 including said cap means having a first end which is frangible and adapted to be pierced by said needle and a second end which is open and adapted to receive at least a portion of said barrel.

3. The syringe assembly of claim 1 including a plurality of first locking means formed on said barrel means,
   a plurality of second locking means formed on said cap means, and
   said first and second locking means adapted to be in locking engagement at a number of relative axial positions of said barrel and said cap means.

4. The syringe assembly of claim 3 including said first locking means having substantially equal spacing between adjacent individual elements thereof, and
   said second locking means having substantially equal spacing between adjacent individual elements thereof.

5. The syringe assembly of claim 3 including the spacing between said individual elements of said first locking means being substantially equal to the spacing between said individual elements of said second locking means.

6. The syringe assembly of claim 5 wherein the spacing between said individual elements of said first locking means being about $\frac{1}{8}$ to $\frac{3}{8}$ inch, and
   the spacing between said individual locking elements of said second locking means being about $\frac{1}{8}$ to $\frac{3}{8}$ inch.

7. The syringe assembly of claim 3 including said hollow barrel being generally cylindrically shaped,
   said cap means being generally cylindrically shaped and of larger diameter than said barrel means, and
   said first and second locking means generally circumferentially oriented and extending less than about 180° the respective circumferences.

8. The syringe assembly of claim 7 wherein
   said first locking means includes a series of integrally formed circumferentially oriented ribs, and
   said second locking means includes a series of integrally formed circumferentially oriented ribs.

9. The syringe assembly of claim 8 wherein
   said first locking means includes a series of generally outwardly projecting ribs, and
   said second locking means includes a series of generally inwardly projecting ribs.

10. The syringe assembly of claim 9 including
    said first locking means ribs being generally aligned with other said ribs in the same locking means.

11. The syringe assembly of claim 9 including
    said second locking means ribs being generally aligned with other said ribs in the same locking means.

12. The syringe assembly of claim 7 including said ribs extending less than about 90° about the respective circumferences.

* * * * *